United States Patent [19]

Tabak

[11] Patent Number: 4,560,536
[45] Date of Patent: Dec. 24, 1985

[54] CATALYTIC CONVERSION WITH CATALYST REGENERATION SEQUENCE

[75] Inventor: Samuel A. Tabak, Wenonah, N.J.

[73] Assignee: Mobil Oil Corporation, New York, N.Y.

[21] Appl. No.: 648,414

[22] Filed: Sep. 10, 1984

Related U.S. Application Data

[62] Division of Ser. No. 526,852, Aug. 26, 1983, Pat. No. 4,487,985.

[51] Int. Cl.$^4$ ................................................. B01J 8/04
[52] U.S. Cl. ..................................... 422/116; 208/70; 208/135; 422/190
[58] Field of Search ............... 585/517, 533, 489, 639, 585/315, 304, 407, 322, 413, 415, 531, 640, 319, 254, 255, 314, 330; 208/138, 71, 70, 255, 135; 422/116, 190, 189, 142, 141, 201; 55/48; 196/46

[56] References Cited

U.S. PATENT DOCUMENTS

| 3,142,545 | 7/1964 | Raarup et al. | 422/190 X |
| 4,133,743 | 1/1979 | Boret et al. | 422/190 X |
| 4,259,294 | 3/1981 | Langhout et al. | 422/190 |
| 4,319,984 | 3/1982 | Pellet et al. | 208/138 |
| 4,433,185 | 2/1984 | Tabak | 585/315 X |

*Primary Examiner*—Richard L. Chiesa
*Attorney, Agent, or Firm*—A. J. McKillop; M. G. Gilman; L. G. Wise

[57] ABSTRACT

A reactor sequencing technique is useful for multi-stage hydrocarbon conversion systems employing a number of fixed bed catalytic reactors at various process temperatures and catalytic activity levels. An apparatus for oligomerizing lower olefins (e.g., $C_2$-$C_6$) is disclosed wherein catalyst partially inactivated in a primary stage is employed to effect conversion at higher temperature in a secondary stage prior to catalyst regeneration.

4 Claims, 7 Drawing Figures

4,560,536

CATALYTIC CONVERSION WITH CATALYST REGENERATION SEQUENCE

This is a divisional of copending application Ser. No. 526,852, filed on Aug. 26, 1983 and now U.S. Pat. No. 4,487,985.

FIELD OF INVENTION

This invention relates to a cyclic apparatus for hydrocarbon conversion especially in the manufacture of gasoline and/or distillate range hydrocarbon fuels. In particular it provides a catalyst regeneration technique for operating an integrated multi-stage plant wherein a crystalline zeolite oligomerization catalyst is employed for converting olefinic feedstocks containing $C_2$–$C_6$ alkenes at elevated temperature and pressure.

BACKGROUND OF THE INVENTION

In the process for catalytic conversion of olefins to heavier hydrocarbons by catalytic oligomerization using an acid crystalline zeolite, such as ZSM-5 type catalyst, process conditions can be varied to favor the formation of either gasoline or distillate range products. At moderate temperature and relatively high pressure, the conversion conditions favor distillate range product having a normal boiling point of at least 165° C. (330° F.). Lower olefinic feedstocks containing $C_2$–$C_6$ alkenes may be converted selectively; however, the distillate mode conditions do not convert a major fraction of ethylene. While propene, butene-1 and others may be converted to the extent of 50 to 95% in the distillate mode, only about 10 to 20% of the ethylene component will be consumed.

In the gasoline mode, ethylene and the other lower olefins are catalytically oligomerized at higher temperature and moderate pressure. However, coking of the catalyst is accelerated by the higher temperature. Under these conditions ethylene conversion rate is greatly increased and lower olefin oligomerization is nearly complete to produce an olefinic gasoline comprising hexene, heptene, octene and other $C_6^+$ hydrocarbons in good yield. To avoid excessive temperatures in the exothermic reactors, the lower olefinic feed may be diluted. In the distillate mode operation, olefinic gasoline may be recycled and further oligomerized, as disclosed in U.S. Pat. No. 4,211,640 (Garwood and Lee). In either mode, the diluent may contain light hydrocarbons, such as $C_3$–$C_4$ alkanes, present in the feedstock and/or recycled from the debutanized product.

In U.S. Pat. Application Ser. No. 481,705, filed Apr. 4, 1983, now U.S. Pat. No. 4,433,185 and incorporated herein by reference, a two stage catalytic process is disclosed for converting lower olefins at elevated temperature and pressure, with unconverted reactant, mainly ethylene, from a first stage being completely converted at higher temperature in a second stage. Although, the same type catalyst (H-ZSM-5) is employed in each stage, significant differences in the operating temperatures and catalyst use contribute to different rates of inactivation, largely due to coking.

The present invention takes advantage of the accelerated aging rate for hydrocarbon conversion catalysts operating under process conditions which produce coke deposits. Increased coking will decrease conversion at a given temperature, and it is conventional practice to increase process temperature to maintain the desired level of conversion. In the two stage olefin oligomerization process contemplated in the preferred embodiment herein, the primary stage feedstock is selectively converted over highly active ZSM-5 type catalyst at moderate temperature and high pressure. Under these conditions $C_3^+$ olefin primary reactants are converted efficiently in major amount to a highly desirable distillate product; however, only a minor amount of ethylene is converted at primary stage temperature.

By recovering unreacted ethylene and other light olefins from the primary stage, a second reactant stream from high temperature conversion can utilize coked catalyst that would no longer be suitable for lower temperature use due to loss of activity.

In order to maintain the MOGD plant in continuous operation, it is necessary to either replace or regenerate spent catalyst periodically. Advantageously, a single reactor can serve the entire multi-stage complex by appropriate sequencing of a plurality of fixed bed reactors. By employing the same type of catalyst bed in similar amount and configuration for each reactor, the same reactor shell can be switched to serve in any of the process positions according to need.

SUMMARY

A technique has been found for multi-stage organic hydrocarbon conversion employing a first moderate lower temperature stage and a second severe high temperature stage in a reactor bank operatively connectable for service in more than one stage as well as in a regeneration loop.

Accordingly, it is an object of this invention to provide a continuous process and apparatus for converting an olefinic feedstock containing ethylene and $C_3^+$ olefins by catalytic oligomerization to produce heavier hydrocarbons in the gasoline or distillate boiling range. This technique provides methods and means for (a) contacting the olefinic feedstock in a first catalytic stage comprising a plurality of serially connected fixed bed reactors with crystalline zeolite oligomerization catalyst at moderate temperature under conditions favorable for conversion of $C_3^+$ olefins to a first reactor effluent stream rich in distillate range hydrocarbons; (b) separating the first reactor effluent stream into a first stream rich in distillate and a second stream rich in ethylene; (c) contacting the ethylene-rich stream from step (b) in a second catalytic stage comprising at least one fixed bed reactor with said crystalline zeolite oligomerization catalyst at substantially higher temperature under conditions favorable for conversion of ethylene and other lower olefins to a second reactor effluent stream rich in olefinic gasoline range hydrocarbons. An improved reactor sequence comprises a cyclic fluid handing technique to connect the first stage serial reactors in operative fluid flow relationship whereby fresh or regenerated catalyst in a terminal reactor stage position receives effluent from a least one preceding first stage reactor operating at moderate temperature, said preceding first stage reactor containing catalyst of less activity than said catalyst in the terminal reactor stage position; sequencing process flow to connect said preceding first stage reactor in said second stage to receive said ethylene-rich stream, increasing temperature in said previously preceding first stage reactor to second stage temperature conditions; removing a second stage reactor containing inactivated catalyst from conversion service, connecting said inactivated catalyst in fluid flow relationship with a catalyst regeneration loop, and regenerating said catalyst in situ; advancing the terminal reactor of the first stage to a preceding serial position in the first stage; and adding a fresh or regenerated catalyst reactor in the first stage terminal position.

THE DRAWINGS

DESCRIPTION OF THE PREFERRED EMBODIMENTS

Conversion of olefins to gasoline and/or distillate products is disclosed, for example, in U.S. Pat. Nos. 3,960,978 and 4,021,502 (Givens, Plank and Rosinski) wherein gaseous olefins in the range of ethylene to pentene, either alone or in admixture with paraffins are converted into an olefinic gasoline blending stock by contacting the olefins with a catalyst bed made up of a ZSM-5 type zeolite. In U.S. Pat. No. 4,227,992 Garwood and Lee disclose the operating conditions for the Mobil Olefin to Gasoline Distillate (MOGD) process for selective conversion of $C_3+$ olefins and only 20% maximum ethene ($C_2=$) conversion. In a related manner, U.S. Pat. No. 4,150,062 (Garwood et al) discloses a process for converting olefins to gasoline components. Typically, the process recycles cooled gas or liquid $C_3$-$C_4$ alkanes from a high-temperature, high-pressure separator downstream of the catalyst bed back into the reaction zone where additional olefins are converted to gasoline and distillate products. If the reaction of the olefins in converting them to distillate and gasoline is allowed to progress in the catalyst stream without any measures taken to prevent the accumulation of heat, the reaction becomes so exothermically accelerated as to result in high temperatures and the production of undesired products.

The oligomerization catalysts preferred for use herein include the shape selective crystalline aluminosilicate zeolites having a silica to alumina ratio of at least 12, a constraint index of about 1 to 12 and acid cracking activity of about 160-200. Representative of the ZSM-5 type zeolites are ZSM-5, ZSM-11, ZSM-12, ZSM-23, ZSM-35 and ZSM-38. ZSM-5 is disclosed and claimed in U.S. Pat. No. 3,702,886 and U.S. Pat. No. Re. 29,948; ZSM-11 is disclosed and claimed in U.S. Pat. No. 3,709,979. Also, see U.S. Pat. No. 3,832,449 for ZSM-12; U.S. Pat. No. 4,076,842 for ZSM-23; U.S. Pat. No. 4,016,245 for ZSM-35 and U.S. Pat. No. 4,046,839 for ZSM-38. The disclosures of these patents are incorporated herein by reference. A suitable catalyst for fixed bed is an HZSM-5 zeolite with alumina binder in the form of cylindrical extrudates of about 1-5 mm.

In order to take advantage of the inventive concept, the preferred feedstock to be changed to the first stage of the integrated system should contain at least 5 mole % ethylene, preferably 10 to 50%, and substantially no hydrogen. A typical olefinic feedstock contains a major fraction (50+ mole %) of combined $C_2$-$C_4$ alkenes with minor amounts of $C_5+$ alkenes. Other volatile hydrocarbons such as low molecular weight paraffins are often found in petroleum refinery streams, such as catalytic cracker by-product depropanizer off-gas. It is an object of the present invention to upgrade lower olefinic hydrocarbons to more valuable liquid fuel products or the like.

OLEFIN CONVERSION PROCESS

Figure 1:
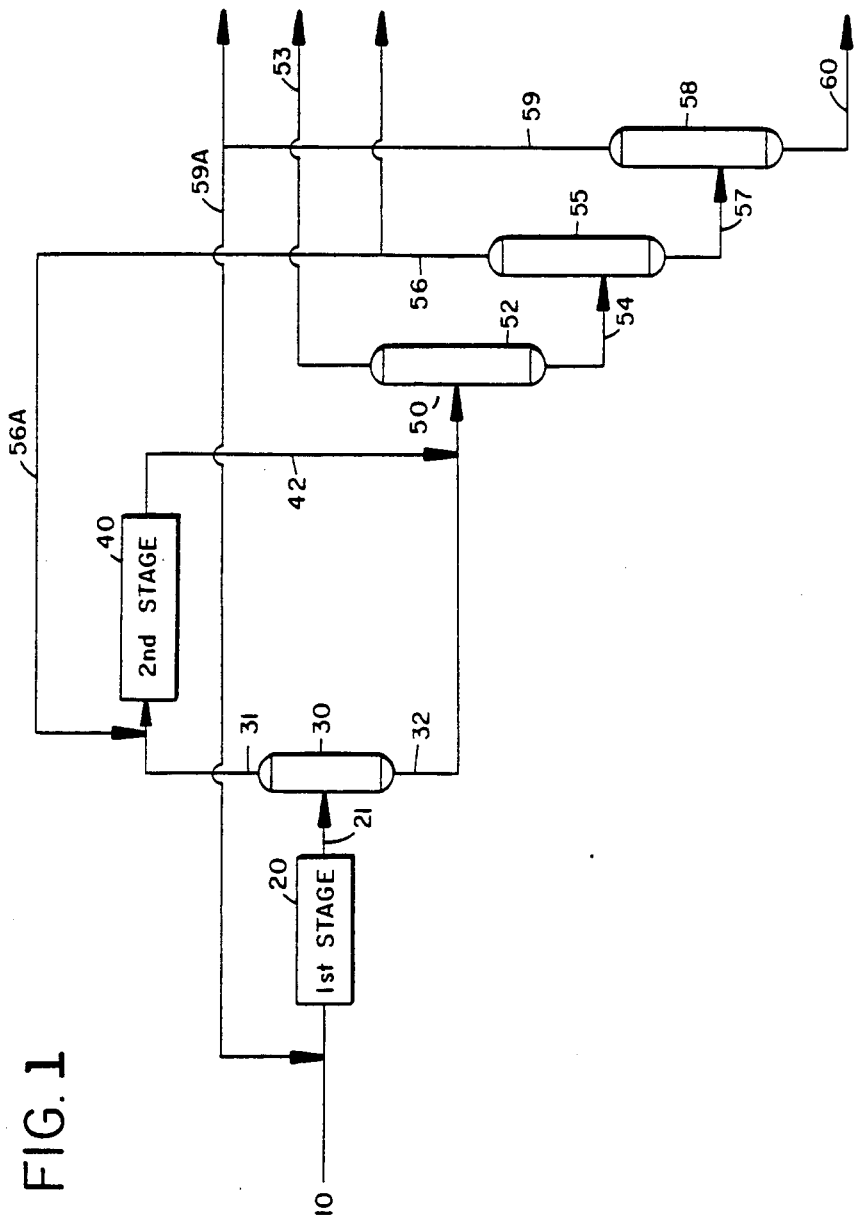
FIG. 1 is a schematic representation of a preferred two stage reactor system and a multi-tower fractionation system.

Referring to the drawing of FIG. 1, the flow sheet shows a preferred process wherein the total olefinic feedstock 10 is charged to a maximum distillate mode first stage unit 20. Here the $C_3+$ olefins are converted to primarily distillate, while $C_2=$ reaction is low, on the order of 10 to 20%. The reactor effluent is then fractionated or flashed in separator 30 to give a pressurized vapor phase (primarily $C_5$ and lower), which is cascaded at a lower pressure to a gasoline mode second stage unit 40. High temperature olefin conversion approaches 100% on reaction to olefinic gasoline with some distillate in the absence of added hydrogen. Both reactor effluents are combined and sent to a common fractionation system 50.

A series of distillation towers include deethanizer column 52, from which $C_1$-$C_2$ off-gas is withdrawn as overhead vapor stream 53. Heavier components in bottoms stream 54 are further fractionated in debutanizer column 55 to provide $C_3$-$C_4$ overhead stream 56. This stream may be recovered as LPG product and/or recycled to the gasoline mode 40 reactor to help control heat of reaction. Debutanizer bottoms stream 57 is further fractionated in splitter column 58 to provide $C_5+$ overhead vapor stream 59 rich in hexenes, octenes or the like. This olefinic gasoline product is recycled to the distillate reactor to help control heat of reaction and further react to distillate, or recovered as usable product. Fractionator bottoms stream 60 consisting essentially of distillate range hydrocarbons boiling above about 165° C. may be used as fuel oil or hydrotreated in known manner to improve its cetane number. Using the combined effluent fractionation system any light distillate produced in the gasoline reactor is recovered as distillate.

Figure 2:
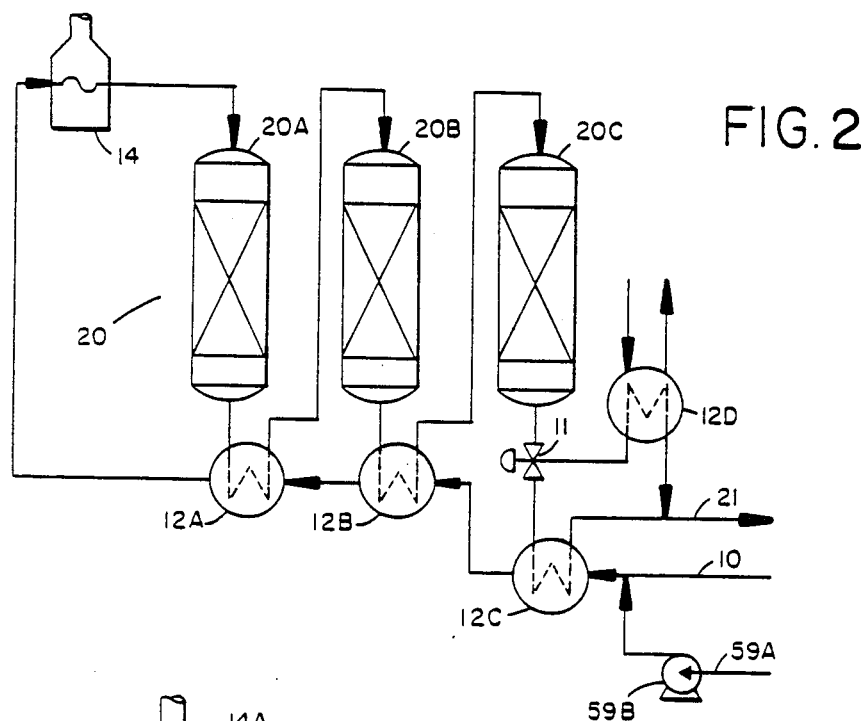
FIG. 2 is a typical olefin conversion reactor system for first stage distillate mode operation.

A typical distillate mode first stage reactor system 20 is shown in FIG. 2. A multi-reactor system is employed with inter-zone cooling, whereby the reaction exotherm can be carefully controlled to prevent excessive temperature above the normal moderate range of about 190° to 315° C. (375°–600° F.). $C_2$-$C_6$ olefinic feedstock is introduced through conduit 10 and carried by a series of conduits through heat exchangers 12A, B, C and furnace 14 where the feedstock is heated to reaction temperature. The olefinic feedstock is then carried sequentially through a series of zeolite beds 20A, B, C wherein at least a portion of the olefin content is converted to heavier distillate constituents. Advantageously, the maximum temperature differential across only one reactor is about 30° C. ($\Delta T \sim 50°$ F.) and the space velocity (LHSV based on olefin feed) is about 0.5 to 2.5. The heat exchangers 12A and 12B provide inter-reactor cooling and 12C reduces the effluent to flashing temperature. An optional heat exchanger 12D may further recover heat from the effluent stream 21 prior to phase separation. Gasoline from recycle conduit 59A is pressurized by pump means 59B and combined with feedstock, preferably at a ratio of about 1-3 parts by weight per part of olefin in the feedstock.

Between stages it is preferred to take advantage of a significant pressure drop by flashing the effluent with a pressure differential of at least 1400 kPa (200 psi) between the first stage and phase separator vessel 30. The first stage is operated at elevated pressure of about 4200 to 7000 kPa (600-1000 psig); however, the partial pressure reaction requirements of propene and butene may dictate higher total pressure where the feed stock contains large amounts of ethene or other gases. Any suitable enclosed pressure vessel can be used as the separator unit, which is operatively connected by conduits 21, 31, 32 in fluid flow relationship to the two stages and fractionation system.

Figure 3:
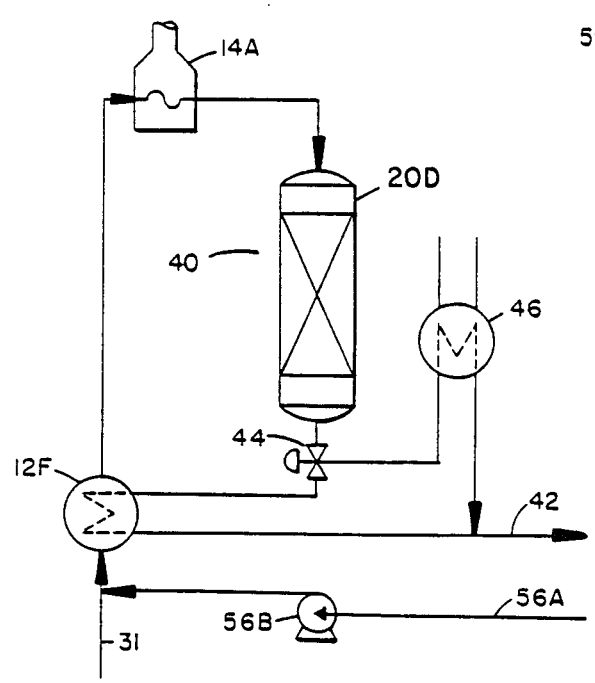
FIG. 3 is a typical second stage reactor system for gasoline mode operation.

The gasoline mode reactor 40 shown in FIG. 3, is relatively simple, since the higher temperature conversion does not require maximum differential temperature control closer than about 65° C. ($\Delta T \sim 120°$ F.) in the approximate elevated range of 285° C. to 425° C. (550°-800° F.). The reactor bed 20D is maintained at a moderate super atmospheric pressure of about 400 to 3000 kPa (50-400 psig) and the space velocity for ZSM-5 catalyst to optimize gasoline production should be about 0.2 to 3 (LHSV). Preferably, all of the catalyst reactor zones in the system comprise a fixed bed down flow pressurized reactor having a porous bed of ZSM-5 type catalyst particles with an acid activity of about 160 to 200.

The overall pressure drop across the system is at least 1500 kPa and it is advantageous to take most of this pressure drop prior to entering the flashing vessel 30, such that the flashing vessel is maintained at a pressure only high enough to allow overhead vapor to cascade into the gasoline mode reactor 40.

Unconverted ethylene and other light gases are passed from the separator through conduit 31, heat exchanger 12F, and furnace 14A to gasoline mode reactor bed 20D. Since this reactor operates at a high differential temperature, ($\Delta T \sim 120°$ F.) the furnace need not be used in normal operation and can be bypassed, with all feed preheat coming from exchanger 12F. The second stage effluent is cooled partially in exchanger 12F and passed through conduit 42 to the fractionation system 50. Optionally, a portion of the hot effluent may be diverted by valve 44 through heat recovery exchanger 46. $C_3$-$C_4$ alkanes of other diluents may be introduced through recycle conduit 56A and pump 56B.

REACTOR SEQUENCING

Figure 4:
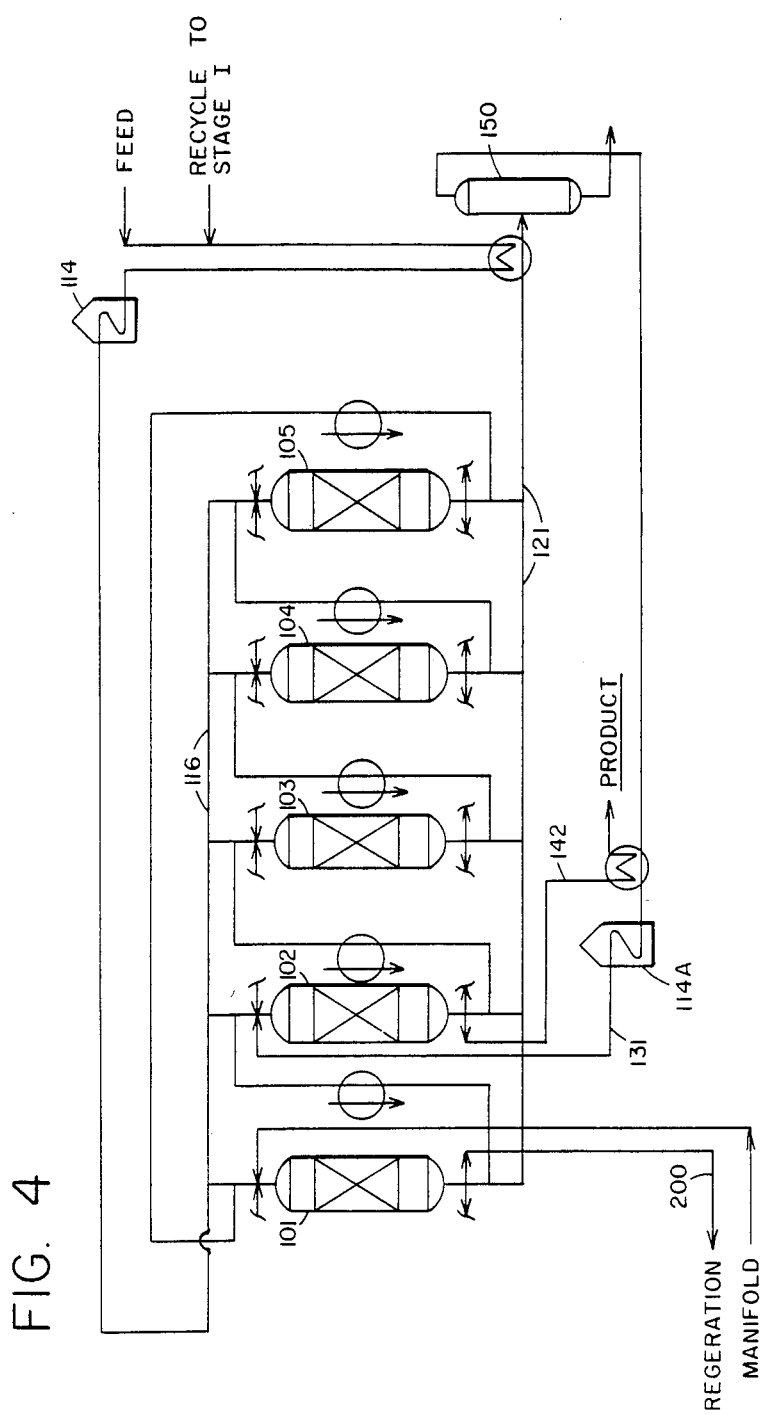
FIG. 4 is a reactor bank layout and simplified piping diagram.
Figure 5:
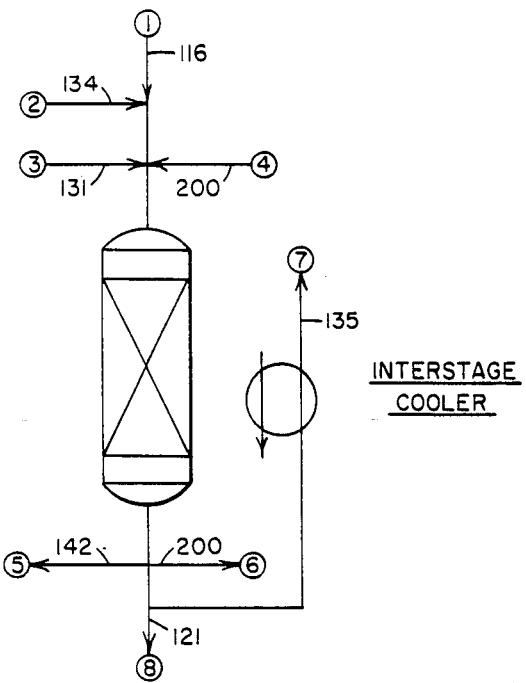
FIG. 5 is a reactor piping diagram.

For sequencing catalyst beds, the most aged catalyst can be used in the high temperature of stage II prior to regeneraton. The advantage of rotating reactors through both Stage I and Stage II loops over a conventional design is the need for only one spare reactor and only one regeneration loop. The multiple reactor configuration shown in FIG. 4 is operatively interconnected via fluid handling means to permit any of the five fixed substantially identical reactors to be placed in service for primary or secondary stage operation or regeneration according to the degree of catalyst coking. A number of reactors 101, 102, 103, 104, 105 are each connectable through suitable valving to feedstock manifold 116, primary effluent manifold 121, secondary feed stream 131, secondary stage effluent outlet 142, and regeneration manifold 200. These connections are shown in detail in FIG. 5, which depicts piping arrangements for a typical single reactor in the complex, which shows the flow lines described above and also the intrastage piping 134,135 to receive partially reacted feedstock from a preceding reactor and passing partially reacted effluent to a succeeding stage. FIG. 4 depicts a preferred two-stage plant to show a possible flow configuration for this system. Because of the large number of valves required, these have not been included in the drawings. However, it is understood that all lines require conventional multiple block valves for safety in handling both hydrocarbons and air.

In the initial cycle described, the feedstock is transported in sequence through reactors A, B, C, (Stage I) and reactor D (Stage II), while reactor E is out of service. The reactors are shifted in sequence as tabulated below.

|         | Stage I |              |      |          |        |
| ------- | ------- | ------------ | ---- | -------- | ------ |
| Cycle # | First   | Intermediate | Last | Stage II | Regen. |
| 1       | A       | B            | C    | D        | E      |
| 2       | B       | C            | E    | A        | D      |
| 3       | C       | E            | D    | B        | A      |
| 4       | E       | D            | A    | C        | B      |
| 5       | D       | A            | B    | E        | C      |
| Repeat  | A       | B            | C    | D        | E      |

Figure 6:
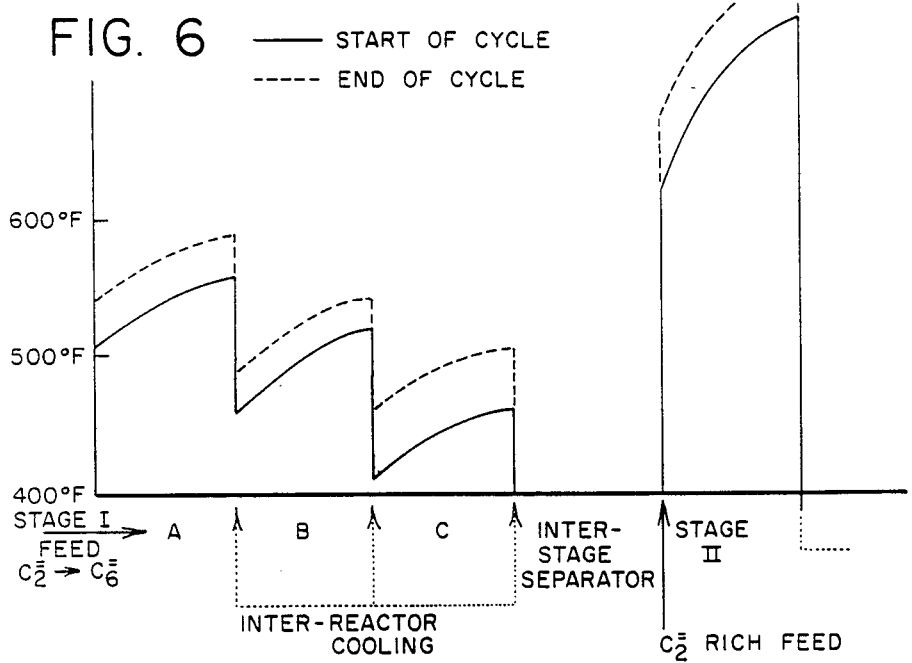
FIG. 6 is a plot of stream temperature vs reactor sequence position.

FIG. 6 is a graphic plot of temperature profile along the vertical axis of a series of fixed bed oligomerization reactors. Olefinic feedstock passed through the first reactor A of Stage I, with temperature increasing adiabatically until cooled to favor distillate-forming. In a similar manner the temperature profile of intermediate reactor B and Stage I last reactor C is depicted. Following interstage separation, the olefinic vapor phase is preheated about 50° C. or more above the first stage maximum temperature to effect complete conversion over the less active Stage II catalyst.

REGENERATION OPERATION

Figure 7:
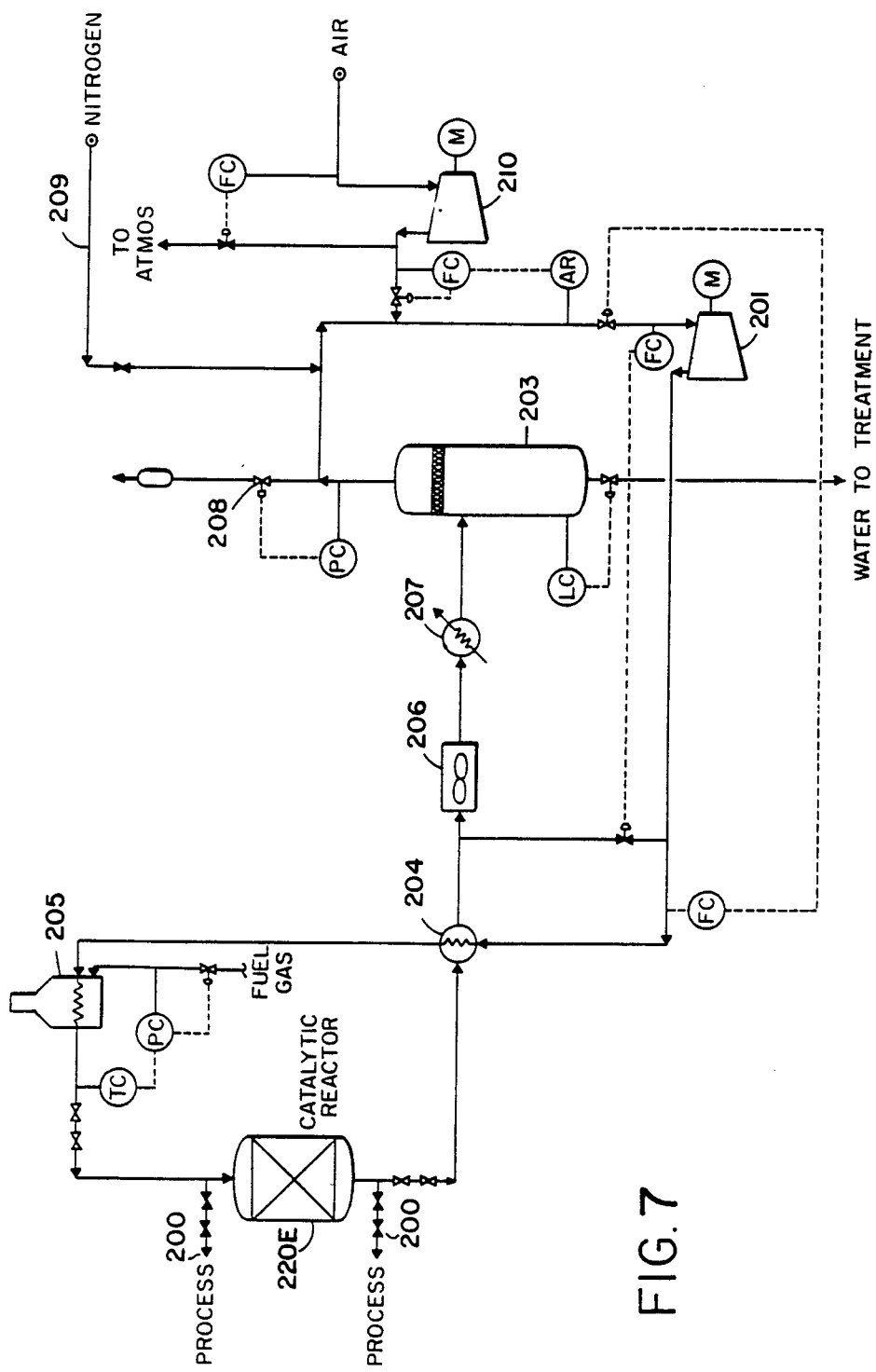
FIG. 7 is a process flow sheet for a typical regeneration loop.

Preferably the ZSM-5 catalyst is kept on stream until the coke content increases from 0% at the start of cycle (SOC) until it reaches a maximum of 30 weight % at end of cycle (EOC) at which time it is regenerated by oxidation of the coke deposits. Typically a greater than 30-day total cycle can be expected between regenerations. The reaction operating temperature depends upon its serial position. The system is operated advantageously (as shown in FIGS. 1-7) by increasing the operating temperature of the first reactor (Position A) from about 250°-290° C. (SOC) to about 270° C.-310° C. (EOC) at a catalyst aging rate of 1°-6° C./day. Primary stage reactors in the second and subsequent positions (B, C, etc.), containing catalyst with less time in stream (i.e. higher catalytic activity, are operated at lower SOC temperature. Operating in such a manner the average reactor temperature for the reactor in position C will generally be less than the average reactor temperature in position B, which will generally be less than the average reactor temperature in position A. Thermodynamically it is advantageous to maintain the primary stage terminal reactor (position C) with fresh catalyst, since this allows a lower average reactor temperature, which will form the product of higher molecular weight oligomer. The aging rate for reactors in positions B and C is about 1°-6° C./day. Aging rates for reactors in all primary stage positions (A, B and C) are adjusted to maintain approximately equal conversion rates. The Stage I end of cycle is signalled when the outlet temperature of the reactor in position A reaches its allowable maximum. At this time the inlet temperature is reduced to start of cycle levels in order to avoid excessive coking over the freshly regenerated catalyst when the regenerated reactor 31E is brought on-line, after having been brought up to reaction pressure with an effluent slip stream. Regeneration of coked catalyst may be effected by any of several procedures. The catalyst may be removed from the reactor of the regeneration treatment to remove carbonaceous deposits or the catalyst may be regenerated in-situ in the reactor. In FIG. 7, a typical regeneration subsystem is shown, wherein the off-stream fixed catalyst bed unit 31D is operatively connected with a source of oxidizing gas at elevated temperature. A programmable logic controller may be employed to control the sequencing of valve operations during all stages of reactor system operation.

The regeneration circuit includes a recycle gas compressor 201 which circulates the regeneration gas. This compressor takes suction from phase separator 203. The gas then passes through the feed/effluent heat exchanger 204 to the regeneration heater 205 and into reactor 220E. Here the catalyst is regenerated by burning off coke, producing $CO_2$ and $H_2O$. Reactor effluent is cooled in the feed/effluent exchanger 204 then in an air cooler 206 and is finally cooled in the trim cooler 207 before entering the separator 203. Gas is released from the separator to maintain system pressure through pressure-response venting means 208. By the time it reaches the separator, water vapor formed during the burn has condensed and is separated from the recycle gas. Because water vapor at high temperatures may damage the catalyst, separator temperature is maintained low (40°-50° C. at 800 kPa) in order to minimize the $H_2O$ partial pressure in the recycle gas returning to the reactor.

At the beginning of the regeneration the system is brought up to pressure with nitrogen from inert gas source 209, the reactor inlet temperature adjusted to about 370° C. and air is injected at the compressor suction by air make-up compressor 210 at a rate controlled to give a maximum oxygen concentration of 0.7% at the reactor inlet. As burning begins, a temperature rise of about 85° C. will be observed. As the burn dies off the inlet temperature is raised to maintain about 455° C. outlet temperature. When the main burn is completed, as evidenced by no temperature rise across the catalyst bed, the temperature is raised over 500° C. and the $O_2$ content to 7.0%. This condition is held at least one hour (or until all evidence of burning has ceased). When the regeneration is complete, the temperature is reduced and the system purged free of $O_2$ with nitrogen. The reactor is then blocked off from the regeneration loop and brought up to reaction pressure with a slip stream from the process reactor effluent line. To reconnect the regenerated reactor in the proper serial position, reactor 220E is then paralleled with the Stage I last reactor. When full flow is established in the regenerated reactor in this position, the last reactor is paralleled with the intermediate Stage I reactor, etc., proceeding sequentially through both stages. Finally the fully coked catalyst bed in Stage II is blocked in, depressured, and repressured with nitrogen, then opened to the regeneration circuit, as unit 220E in FIG. 7. Thus each reactor will move from position C to position B to position A before being taken off-line for catalyst regeneration.

It is preferred to have at least three Stage I adiabatic reactors in continuous service; however, the $\Delta T$ becomes smaller with increased numbers of serial reactors and difficulties may be encountered in exploiting the reaction exotherm for preheating reactor feed. A smaller number of serial reactors in the system would require much greater recycle to control the reaction exotherms from catalytic oligomerization.

The concept of moving reactors through a programmed sequence may have value for processes where different stages operate at significantly different temperatures, or where equilibrium would be favored by operating with different temperatures through a set of reactors.

Various modifications can be made to the system, especially in the choice of equipment and non-critical processing steps. While the invention has been described by specific examples, there is no intent to limit the inventive concept as set forth in the following claims.

What is claimed is:

1. An integrated multi-stage system for catalytic conversion of organic compounds comprising a bank of fixed bed catalytic reactors operatively connected to be placed sequentially in selected system stage positions or a regeneration loop;

means for feeding a first reactant stream to a primary stage comprising at least one moderate temperature reactor containing active catalyst;

means for feeding a second reactant stream to a secondary stage comprising at least one higher temperature reactor containing significantly inactivated catalyst previously used in the primary stage at lower temperature;

fluid handling means for sequentially replacing a primary stage reactor containing partially inactivated catalyst with a reactor from the reactor bank containing fresh or regenerated catalyst, while maintaining continuous conversion in the system;

means for advancing at least one replaced primary stage reactor containing partially inactivated catalyst to the secondary stage at higher temperature for conversion of the second reactant stream; and means for regenerating inactivated catalyst in a reactor removed from secondary stage service in a separate regeneration loop, while maintaining continuous conversion in the multi-stage system.

2. A cyclic system for catalytic converting of hydrocarbon feedstock which comprises:

a plurality of catalyst reactor zones comprising fixed bed downflow pressurized reactors having a porous bed of conversion catalyst particles;

first stage plural serial reactor means for contacting the feedstock in a first catalyst zone at moderate temperature under conditions favorable for conversion of a first reactor stream;

means for separating the first stage effluent stream into a first product stream and a second reactant stream containing initially unreacted hydrocarbons;

second stage reactor means for contacting the second reactant stream from the separation means in a second catalyst zone containing said conversion catalyst at elevated temperature under conditions favorable for conversion of the second reactant to provide a second reactor effluent stream;

cyclic fluid handling means for connecting the first stage serial reactors in operative fluid flow relationship whereby fresh or regenerated catalyst in a terminal reactor stage position receives effluent from at least one preceding first stage reactor operating at moderate temperature, said preceding first stage reactor containing catalyst of less activity than said catalyst in the terminal reactor stage position;

means for sequencing system flow to connect said preceding first stage reactor in said second stage to receive the second reactant stream;

means for increasing temperature in said previously preceding first stage reactor to second stage temperature conditions;

means for removing a second stage reactor containing inactivated catalyst from conversion service and connecting said inactivated catalyst in fluid flow relationship with a catalyst regeneration loop, and means for regenerating said catalyst in situ;

means for advancing the terminal reactor of the first stage to a preceding serial position in the first stage; and means for adding a fresh or regenerated catalyst reactor in the first stage terminal position.

3. The system of claim 2 wherein the first and second stage reactors contain an acid ZSM-5 type catalyst.

4. The system of claim 3 comprising fixed bed down flow pressurized reactors having a porous bed of ZSM-5 type catalyst particles with an acid activity of about 160 to 200.

* * * * *